US00PP18037P3

(12) United States Plant Patent
Baars

(10) Patent No.: US PP18,037 P3
(45) Date of Patent: Sep. 18, 2007

(54) MUSHROOM VARIETY NAMED 'SPOPPO'

(50) Latin Name: *Pleurotus ostreatus*
Varietal Denomination: Spoppo

(75) Inventor: Johannes Jacobus Petrus Baars, Maasbree (NL)

(73) Assignee: Praktijkonderzoek Plant & Omgeving B.V., Wageningen (NL)

( * ) Notice: Subject to any disclaimer, the term of this patent is extended or adjusted under 35 U.S.C. 154(b) by 0 days.

(21) Appl. No.: 11/176,960

(22) Filed: Jul. 7, 2005

(65) Prior Publication Data

US 2006/0010549 P1 Jan. 12, 2006

(30) Foreign Application Priority Data

Jul. 7, 2004 (QZ) ..... PBR 20041334

(51) Int. Cl.
*A01H 15/00* (2006.01)

(52) U.S. Cl. ..... Plt./394

(58) Field of Classification Search ..... Plt./394
See application file for complete search history.

*Primary Examiner*—Anne Marie Grunberg
*Assistant Examiner*—Louanne Krawczewicz Myers
(74) *Attorney, Agent, or Firm*—The Webb Law Firm

(57) ABSTRACT

'Spoppo' is a new variety of oyster mushroom that produces no spores and has well-developed fleshy caps.

8 Drawing Sheets

CROSS REFERENCE TO RELATED APPLICATION

The present application claims priority to European Community Plant Variety Rights Application No. 2004/1334, filed Jul. 7, 2004, which is herein incorporated by reference.

Botanical classification: *Pleurotus ostreatus.*

Varietal denomination: 'Spoppo'.

BACKGROUND OF THE INVENTION

The present invention comprises a new and distinct cultivar of mushroom of the species *Pleurotus ostreatus* known by the varietal name 'Spoppo'. The new variety was discovered in Horst-America, The Netherlands. The purpose of the breeding program was to develop a sporeless strain of oyster mushroom. The new variety has been trial and field tested and has been found to retain its distinctive characteristics and remain true to type through successive propagations.

DESCRIPTION OF THE DRAWINGS

The accompanying photographic drawings illustrate the new variety, with the color being as nearly true as is possible with color illustrations of this type.

DETAILED DESCRIPTION OF THE INVENTION

Figure 7:
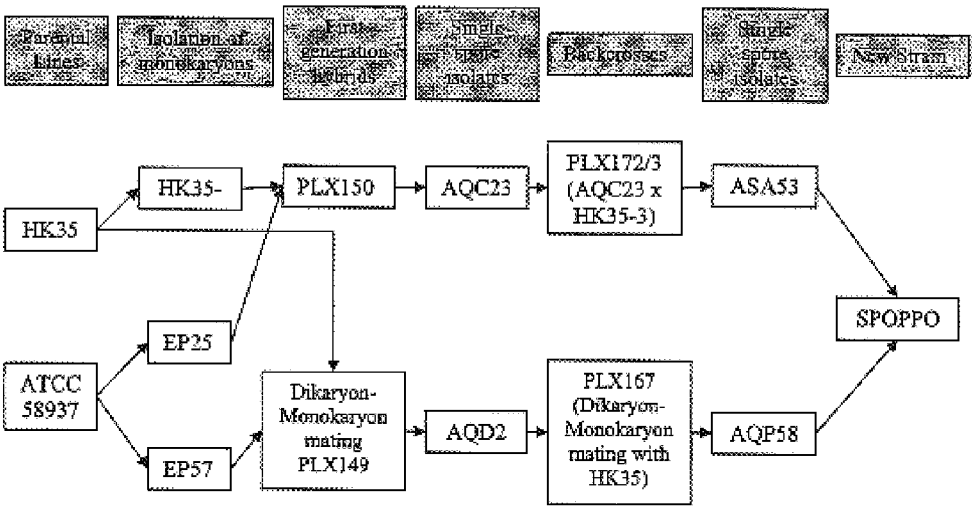
FIG. 7 illustrates the breeding schematic of the new variety.
Figure 8:
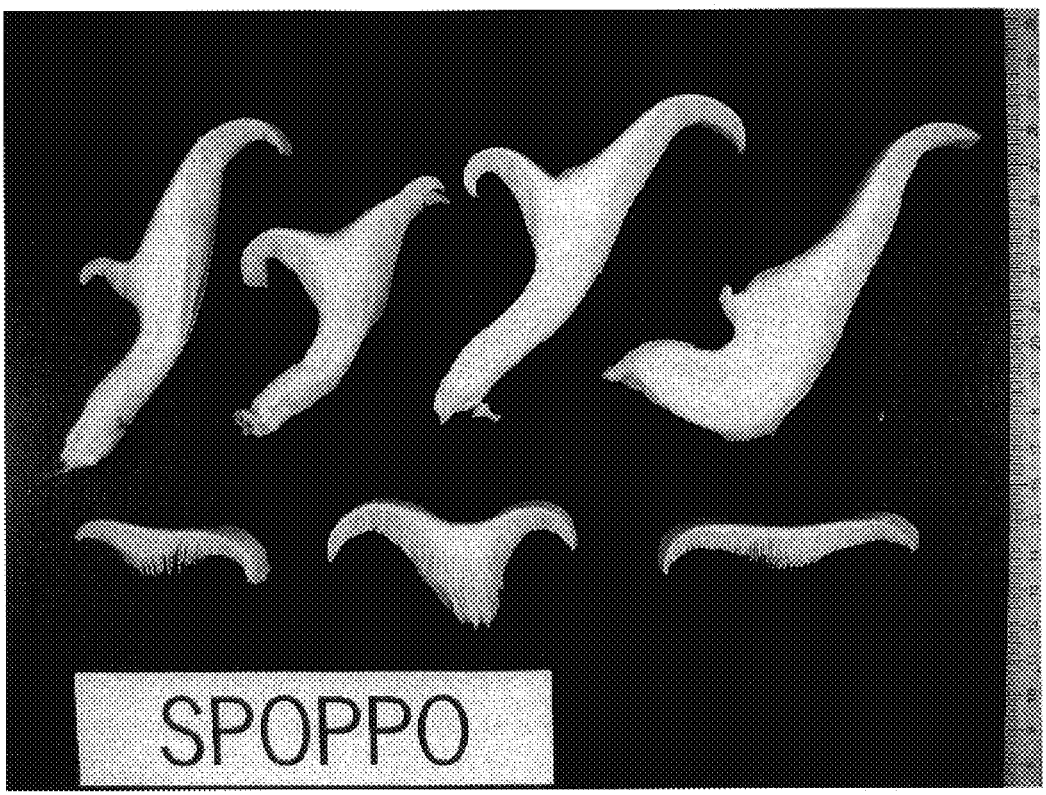
FIG. 8 shows the new variety sliced transversely.

The following detailed description sets forth the breeding procedures and the characteristics of the new cultivar. As shown in FIG. 7, in breeding the new variety, parental lines were isolated from HK35 (female parent) (unpatented) and ATCC 58937 (male parent) (unpatented). Each of the parental lines of the former strain was mated with a different parental line of the latter strain. Offspring was used to find linkage of genetic marker to the "sporeless" trait. The trait was subsequently introgressed in both parental lines of HK35 by repeated backcrosses. Finally, both recombinant parental lines were intercrossed resulting in a sporeless commercial strain. The vegetative mycelium is maintained both on agar slants and in a vapour phase of liquid nitrogen.

The new variety is similar in shell-shaped morphology, mushroom yield and well-developed flesh to HK35, but it produces no spores like ATCC 58937. Unlike HK35 which produces spores on its basidia, 'Spoppo' has sporeless basidia like 'Somycel 3210' (U.S. Pat. No. 4,658,083), but has shell-shaped, well-developed fleshy mushrooms unlike 'Somycel 3210'. Further, 'Spoppo' has well-developed fleshy and heavy, shell-shaped mushrooms that differ from ATCC 58937 which are small, funnel-like mushrooms. Further, unlike 'Somycel 3210', the new variety has not axial symmetry and no positive geotropism. Characteristics that distinguish 'Spoppo' from other varieties known to the breeder include:

Basidia produce no spores

Well developed fleshy and heavy caps

Shell-shaped mushrooms

Botanical Data Collection Conditions and Standards

The color standard used in the present application is the L*a*b* method (also designated as CIE.LAB or CIE-L*a*b*) defined by "Commission International de l'Eclaire" in 1976. The location where measurements were made was Horst-America, The Netherlands. Light conditions where measurements were made were by artificial light provided by a Minolta Chroma Meter type CR-200.

Growth Conditions and Reproduction

The oyster mushrooms were grown on fermented wheat straw that is packed into 17–18 kg blocks that are wrapped in micro-porous plastic foil. Before packaging, the wheat straw substrate was inoculated with spawn at 25–30 liters per 1000 kg of substrate. The yield is variable, as with all mushroom growing. The yield varied between 150 kg and 250 kg per 1000 kg of substrate.

For spawn, usually grain is used. This grain is moisturized and sterilized. Subsequently, this grain is inoculated with a pure vegetative culture of a fungus that can produce edible mushrooms. The colonization of the inoculated grains is usually done in sterile plastic bags with air filters that are incubated at suitable temperatures. After complete colonization and as the manner in which 'Spoppo' was asexually reproduced in The Netherlands, this spawn is used to inoculate substrate.

Spores are not used to produce the mushrooms. Similar to plants, spores represent the offspring of a mushroom and, hence, are the next generation that differs from the parental line. All fungal lines are maintained vegetatively and thus a lack of spores is no problem at all.

Sporeless strain ATCC 58937 is a dikaryotic fungus (two separate nuclei of opposite mating type in each cell). By protoplasting vegetative mycelium of the strain, protoclones were obtained (each derived from a single regenerated protoplast) of both parental types (each containing one type of nucleus). When these lines with opposite mating type are crossed, the original strain ATCC 58937 is restored. Evidence exists that each parental line carries a recessive mutation responsible for sporelessness.

Crosses of each parental line of ATCC 58937 with a parental line of a commercial strain, result in a normally sporulating strain. The offspring of both crosses were used to study segregation of markers and the sporeless trait. Data were linked to identify markers linked to the sporeless trait. The trait was subsequently introduced in both parental monokaryons of the commercial strain by repeated backcrossing and selection for the trait. This so called introgression of traits restored most of the original genetic make-up of each parental monokaryon of the commercial line and reduced the introduced donor genome to relevant parts that harbor the trait. As a final step, the introgressed parental lines were mated resulting in a non-sporulating strain similar to the sporulating commercial strain.

Botanical description:

Numbers of days from beginning of development to peak development: The start of pinning (first primordial formed) up to the harvest time varies between 5 and 6 days.

Age of described plant: Oyster mushrooms are generally produced within 5 weeks after inoculation of the straw substrate. The Oyster mushrooms are produced as a bundle of mushrooms varying in size. This limits the possibilities for a uniform description of the mushrooms.

Cap:

*Shape.*—Mushrooms are fleshy, soft, without spores on the gills, uplifted infundibuliform, with a generally excentric attached stipe. Specifically, immature caps are shell formed on a relatively thick stipe. The stipe is attached more or less excentric. Mature caps are also shell formed and the stipe is attached excentric. At the optimal moment of harvest, the cap margin is curved slightly downward. Further, the rim is smooth and may be slightly waved.

*Diameter.*—Range: The diameter of the caps of the mushrooms of strain SPOPPO varies between 35 and 180 mm. Average: Average diameter is 80.1 mm (st. dev. 23.2 mm, n=159).

Figure 1:
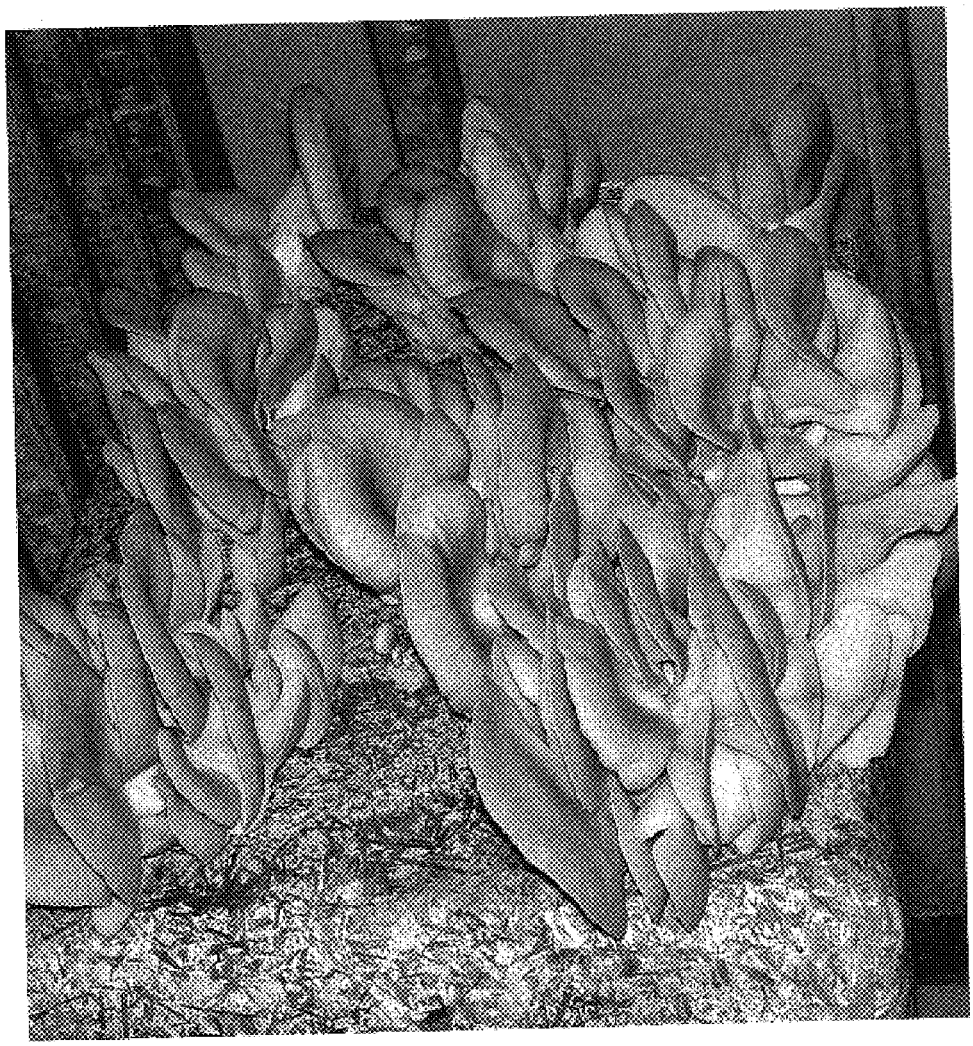
FIG. 1 shows a plurality of 'Spoppo' mushrooms emerging from their growth medium.
Figure 2:
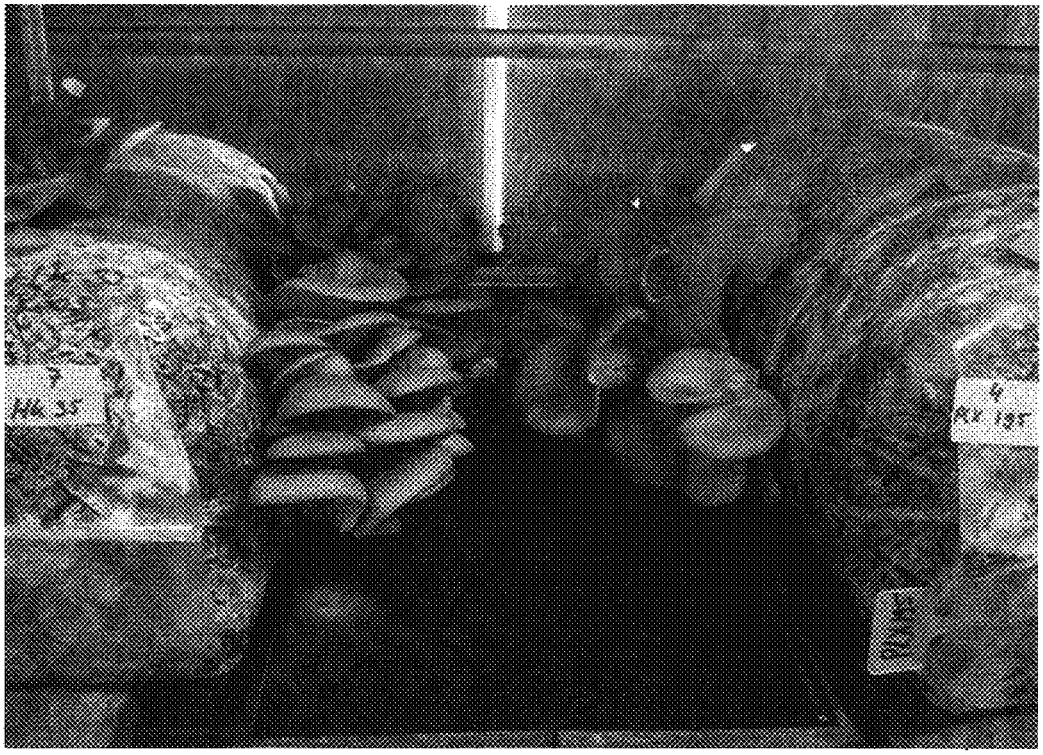
FIG. 2 shows a comparison between 'Spoppo' on the right and HK35 on the left.
Figure 3:
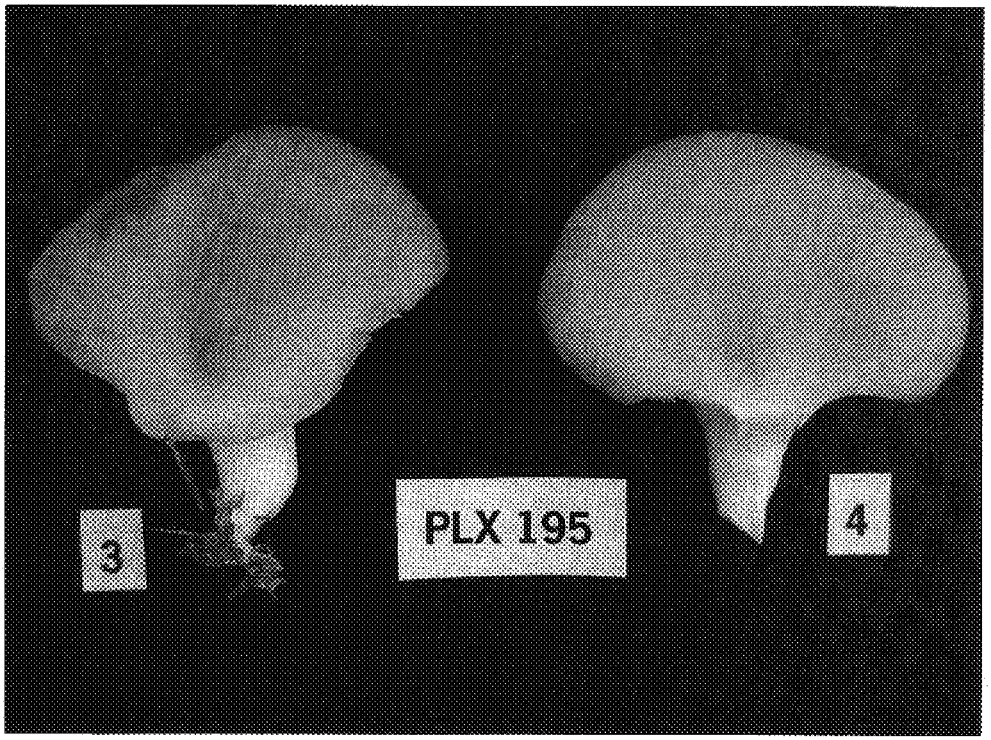
FIG. 3 is an upper side cap comparison between 'Spoppo' on the right and Mushroom #3 on the left.
Figure 4:
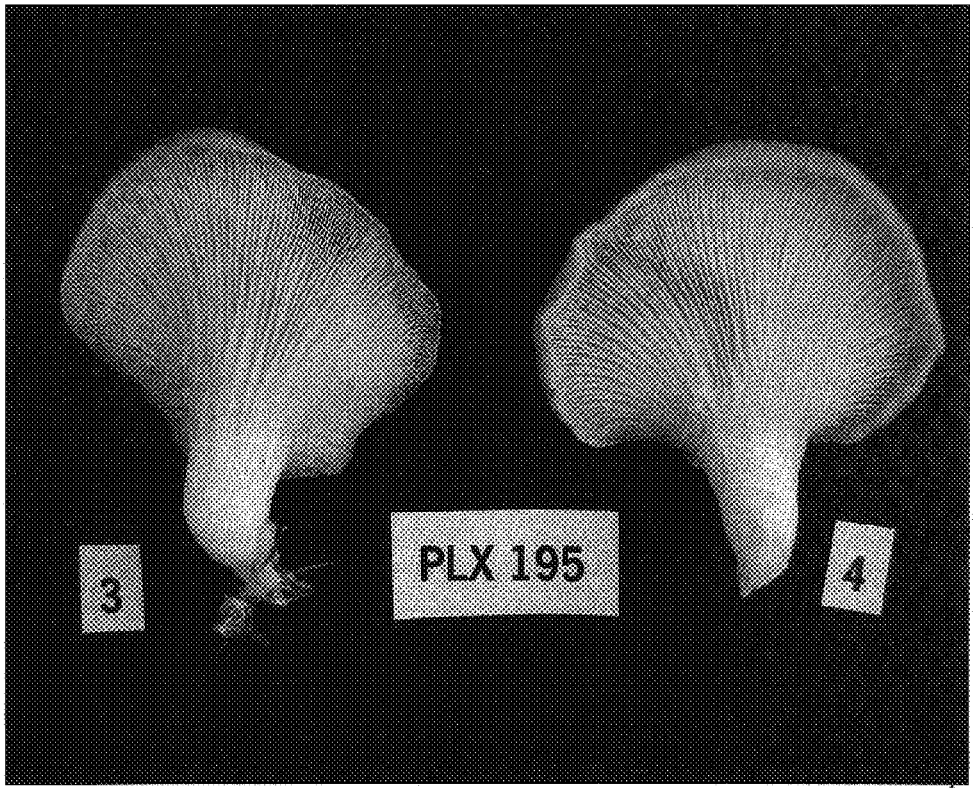
FIG. 4 is a lamellae comparison between 'Spoppo' on the right and Mushroom #3 on the left.
Figure 5:
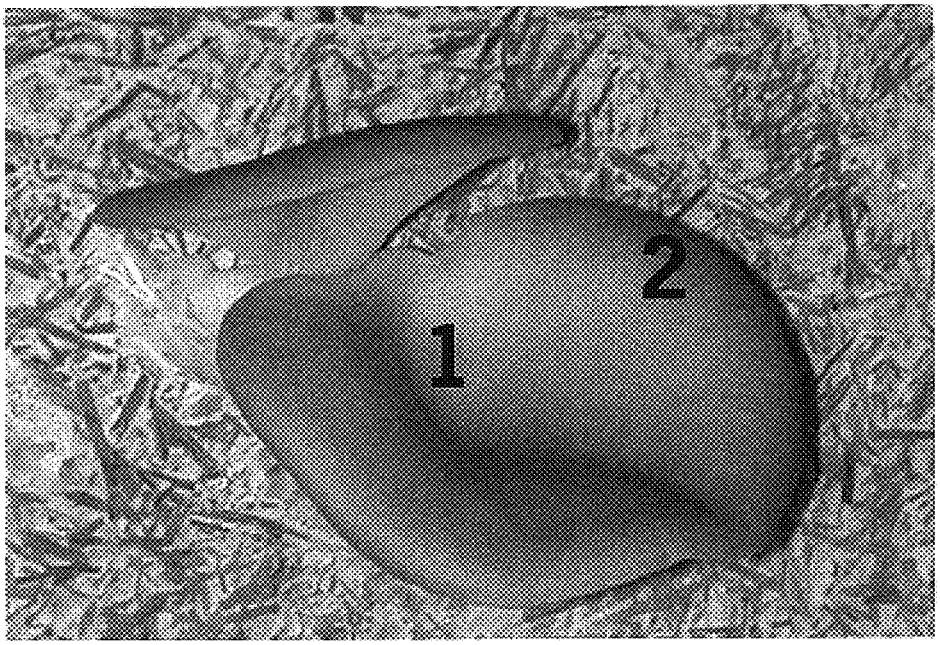
FIG. 5 indicates where the color of the upper side of the 'Spoppo' mushrooms was measured at designated location 2. Designated location 1 does not have any significance in this image.

*Color.*—Mature: L: 64.11 (st. dev. 7.55), a: 3.59 (st. dev. 0.87), b: 13.10 (st. dev. 1.81) (see FIG. 1). Immature: The color of immature mushrooms (buttons) was measured using a Minolta Chromameter according to the CIELAB system as soon as they reached a diameter of 8 mm minimum. L varies between 37.49 and 51.78 (average 45.97, st. dev. 4.41, n=10) "a" varies between 2.39 and 5.39 (average 4.61, st dev. 0.82, n=10) "b" varies between 8.99 and 12.99 (average 11.11, st. dev. 1.55, n=10).

*Flesh color.*—The color of the mushroom flesh was measured on a longitudinal cut mushroom, using a Minolta Chromameter according to the CIELAB system. L value varies between 80.29 and 92.50 (average 87.35, st. dev. 3.55, n=26) "a" value varies between 0.14 and 1.23 (average 0.80, st. dev. 0.30, n=26) "b" value varies between 3.59 and 10.46 (average 6.38, st. dev. 1.51, n=26)

Figure 6:
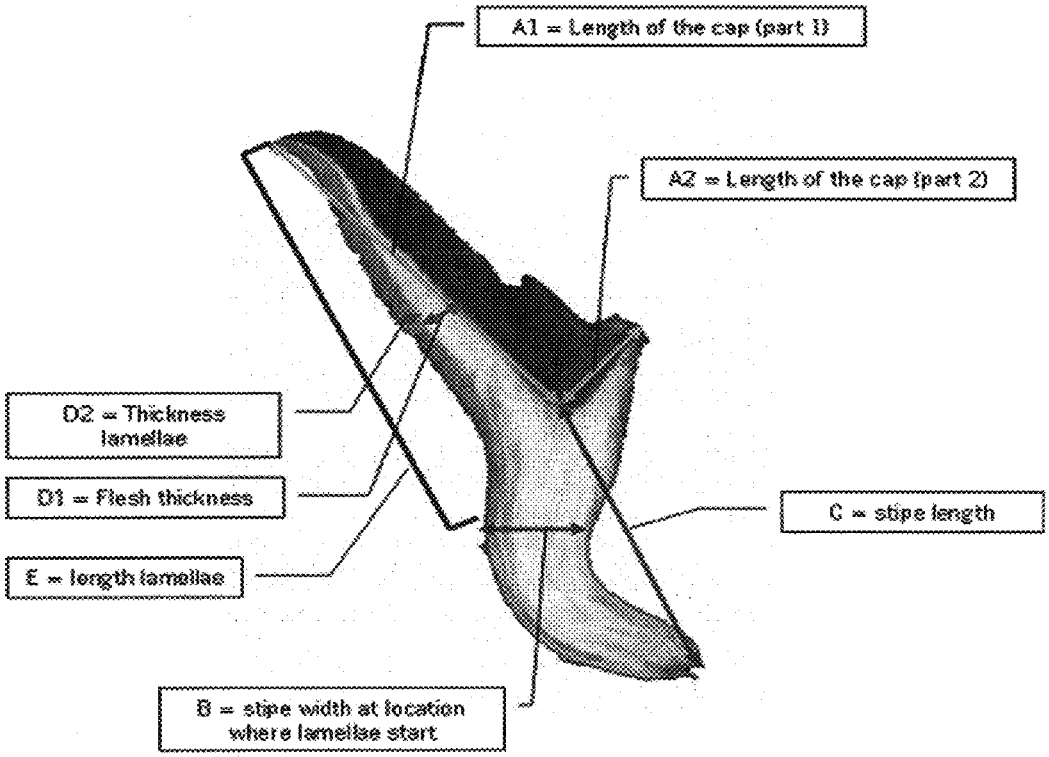
FIG. 6 indicates where the dimensions of 'Spoppo' were measured.

*Flesh thickness/cap thickness.*—Mature: Flesh thickness ranges from 1 to 7 mm (thickness of lamellae excluded; D1 in FIG. 6) and 5 to 17 mm (thickness of lamellae included; D2 in FIG. 6).

*Color designation of bruising/cutting.*—Change of color after cutting the mushroom was measured on the same mushrooms as used for measuring the "Flesh Color" above. Cut Oyster mushrooms were incubated in a humid chamber for 2 hours at room temperature. Subsequently, color of the flesh was determined using a Minolta Chromameter according to the CIELAB system. L value varies between 78.70 and 92.99 (average 88.12, st. dev. 3.35, n=26) "a" value varies between 0.08 and 1.54 (average 0.83, st. dev. 0.27, n=26 "b" value varies between 3.72 and 8.12 (average 5.84, st. dev. 1.07, n=26). There was only a very small change in color compared to the color of freshly cut Oyster mushroom. Texture: No scales present, the cap is smooth and fleshy.

*Gills.*—Arrangement and Attachment: The lamellae are long decurrent and radiate from the stipe outward to the margin of the cap. Intermediate lamellae start at different points on the cap and radiate from that point outward to the margin of the cap. The length of the lamellae varies between 22 and 165 mm (average 69.3 mm, st. dev. 25.0 mm, n=159). The thickness or width of the lamellae varies between 1 and 12 mm (average 7.0 mm, st. dev. 1.6, n=159). On a cross section of the cap, on average, 13.7 lamellae are placed adjacent per cm (st. dev. 1.3, n=20). This is how the gills are spaced. Color designation: The color of the lamellae was measured using a Minolta Chromameter according to the CIELAB system. L varies between 73.75 and 81.42 (average 78.51, st. dev. 2.05, n=21 "a" value varies between 0.00 and 0.92 (average 0.25, st. dev. 0.25, n=21 "b" value varies between 7.92 and 12.43 (average 9.37, st. dev. 1.24, n=21).

Stipe/stem:

*Placement.*—The mushrooms are uplifted infundibuliform with an excentric attached stipe.

*Shape.*—The stalk is bent around the bottom and small. It becomes broader near the cap.

*Size.*—The length of the stipe varies from 10 to 110 mm (average 54.8 mm, standard deviation 17.9 mm, number of observations 159). The thickness of the stipe varies from 7 to 28 mm (average 15.5 mm, standard deviation 4.5 mm, number of observations 159).

*Color.*—The color of the stem was measured using a Minolta Chromameter according to the CIELAB system. L varies between 90.26 and 91.40 (average 90.83, st. dev. 1.1, n=21) "a" varies between 0.67 and 0.83 (average 0.75, st. dev. 0.24, n=21) "b" value varies between 6.52 and 6.60 (average 6.56, st. dev. 0.2, n=21).

*Pubescence.*—Amount: The stipe is predominantly smooth, with a very light amount of pubescent at the base of the stipe. Color: White.

Spores: None present.

Veil: No veil present.

Odor: Typical fungus odor with a light smell of aniseed.

General:

Disease resistance: Not determined.

Shipping quality: Spawn can be stored (for up to 3 months) and shipped at 4° C. Harvested mushrooms can be stored at 4° C. for less than two weeks.

Temperature tolerance: Between 0 and 30° C.

I claim:

1. A new and distinct variety of *Pleurotus ostreatus* mushroom as described and illustrated.

* * * * *